United States Patent
Herskovitz

Patent Number: 5,360,009
Date of Patent: Nov. 1, 1994

[54] SPIROMETER MOUTHPIECE

[75] Inventor: Stuart Herskovitz, Dix Hills, N.Y.

[73] Assignee: Qosina Corp., Edgewood, N.Y.

[21] Appl. No.: 930,853

[22] Filed: Aug. 14, 1992

[51] Int. Cl.⁵ .............................................. A61B 5/08
[52] U.S. Cl. .................................................. 128/725
[58] Field of Search ............... 128/725, 716, 726, 729, 128/763, 767, 768, 769, 727, 728, 730, 724, 718–720, 200.11, 200.12, 207.14, 911, 912; 602/13, 63, 901, 905; 606/108, 109, 192; 138/119

[56]  References Cited
U.S. PATENT DOCUMENTS

| | | | |
|---|---|---|---|
| 3,721,269 | 3/1973 | Choate et al. | 138/119 |
| 4,508,116 | 4/1985 | Duncan et al. | 128/203.28 |
| 4,694,827 | 9/1987 | Weiner et al. | 606/192 |
| 4,946,430 | 8/1990 | Kohmann | 493/58 |
| 5,080,529 | 1/1992 | Watanbe et al. | 138/119 |
| 5,163,424 | 11/1992 | Køhnke | 128/205.13 |
| 5,196,024 | 3/1993 | Barath | 606/192 |

Primary Examiner—Lee S. Cohen
Assistant Examiner—Marianne H. Parker
Attorney, Agent, or Firm—McAulay, Fisher, Nissen, Goldberg and Kiel

[57] ABSTRACT

A disposable spirometer mouthpiece comprises a resilient tubular member, having inner and outer surfaces and a defined wall thickness, the wall of the tubular member having first and second longitudinal zones of reduced thickness and thus reduced strength which allows the spirometer mouthpiece to be collapsed into a flat state for packaging and storage. Preferably, the tubular member is resilient, such that when released from a package, the resilience of the tubular member allows it to resume an essentially cylindrical shape for testing. After testing, the mouthpiece is disposed of and because of reduced zones of thickness, the mouthpiece is easily collapsed to its flat state by the weight of other waste to minimize disposal space.

5 Claims, 2 Drawing Sheets

SPIROMETER MOUTHPIECE

TECHNICAL FIELD

This invention relates to a tube used as a disposable spirometer mouthpiece and more particularly to a collapsible spirometer tube for improved storage efficiency.

BACKGROUND

A spirometer is a device used to provide an indication of lung capacity by measuring a complete exhaled breath. Typically, the spirometer has a mouthpiece connected via a hose to means to measure the volume of exhaled air. The person places his mouth over the mouthpiece and exhales through the hose to obtain a lung capacity measurement.

Typically, the mouthpiece is a separate disposable tube, commonly made of cardboard. The tube is fairly rigid to prevent collapse during testing and also to assist in obtaining a proper seal when mated with a socket in the spirometer hose. In U.S. Pat. No. 3,749,087, a disposable mouthpiece is shown which has a cylindrical construction and has an enlarged portion insertable into an interface chamber and a reduced diameter portion usable as a mouthpiece. The mouthpiece is specialized in that it is manufactured with an integral container which acts as a bladder to accept a breath and displace air in a spirometer chamber to obtain the lung capacity measurement. Such a mouthpiece is costly to produce, and is quite bulky to store. Additionally, since the tube is fairly rigid, it consumes substantial space on disposal.

SUMMARY OF THE INVENTION

It is an object of the present invention to provide a spirometer mouthpiece which is sturdy for testing but is collapsible into a flat form when stored prior to use and when disposed.

It is a further object to provide a spirometer mouthpiece which is easily packaged in flat form for assuring sterility.

It is yet another object to provide a spirometer mouthpiece which is easy to manufacture at low cost.

These and other objects of the present invention are achieved by providing a disposable spirometer mouthpiece for directing air into a lung capacity measuring apparatus, the mouthpiece comprising an elongated cylinder having a pair of longitudinally extending zones of reduced thickness, the zones being approximately 180° apart. A first end of the mouthpiece is adapted for attachment with a mating receptacle in a spirometer hose. A second end is adapted for use as the mouthpiece. The zones of reduced thickness, disposed at about 180° apart, allows the cylinder to collapse into a flat form in response to light pressure which reduces the storage and disposal volume of the spirometer mouthpiece. Preferably, the zones comprise a pair of grooves formed in the side wall of the cylinder, each groove being at a depth of up to 80% of the wall thickness. Preferably, each spirometer tube is individually vacuum packed in a flat sterilizable shrink wrap package. This allows a plurality of spirometer tubes to be stored in a flat form without consuming substantial storage space. When used, the vacuum seal is broken, the container is open and the tube, preferably produced of a resilient material, has sufficient resiliently to spring into its cylindrical testing form. Light pressure may be applied to the tube to assure a snug fit in the hose receiving socket. Such pressure also easily collapses the mouthpiece on disposal. Utilizing the invention, a collapsible spirometer mouthpiece is provided which has sufficient strength for testing but is easily collapsible for minimizing storage and disposal requirements.

BRIEF DESCRIPTIONS OF THE DRAWINGS

DETAILED DESCRIPTION OF THE INVENTION

Figure 1:
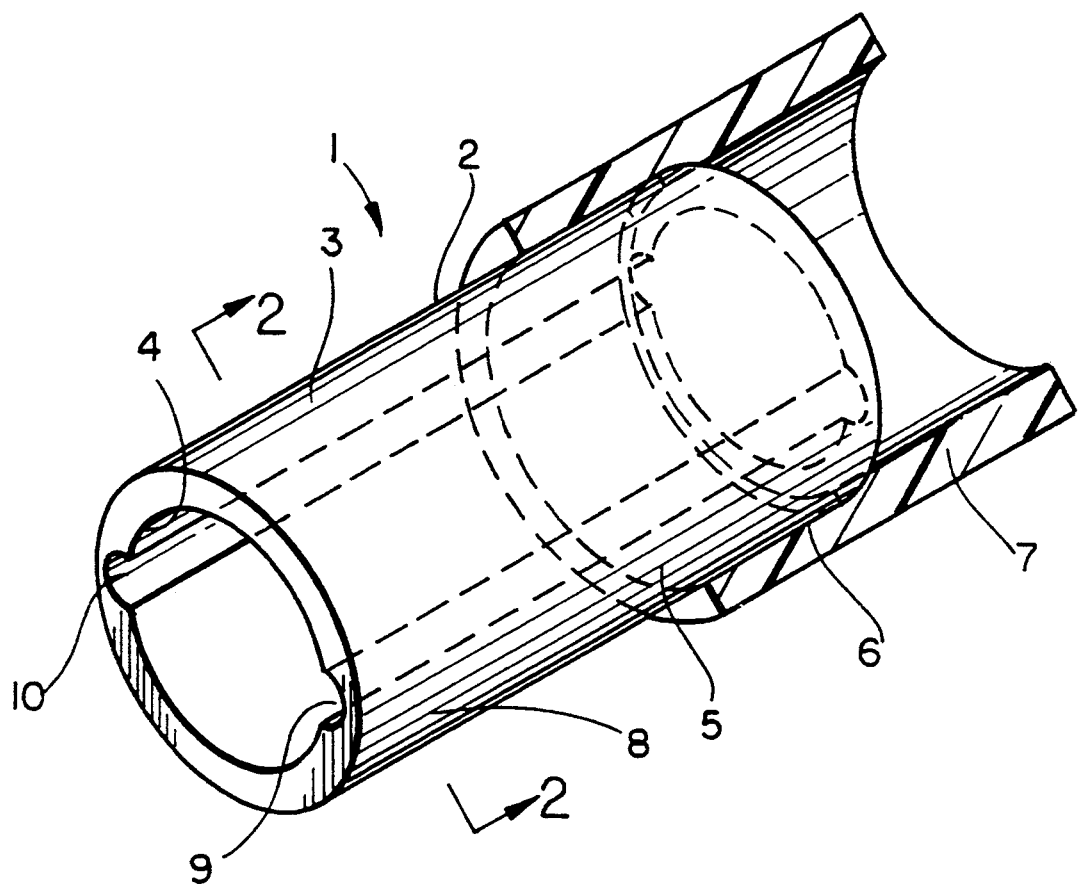
FIG. 1 is a perspective view of a spirometer mouthpiece of the present invention.

Referring to FIG. 1, a spirometer mouthpiece 1 has a cylindrical body 2 with an outer surface 3 and an inner surface 4. The body has a wall thickness defined by the distance between the inner and outer surfaces. The body 2 has a first end 5 which fits within a mating socket 6 in a spirometer hose 7, shown partially in FIG. 1. The spirometer hose is connected to a spirometer apparatus, not shown. Of course, any conventional spirometer apparatus may be used with the present invention. Also, a simple socket fit is shown for illustrative purposes. Additionally, other structures such as enlarged or narrowed portions or a keyed end structure may be incorporated into the mating end to adapt to various spirometer devices directly or to hoses, without varying from the invention.

Preferably, the first end 5 fits snugly within the socket to provide an airtight fit. Such a fit is necessary to assure that all air passing through the tube enters the spirometer apparatus and is not discharged through leaks in the seal. When a socket fit is utilized, it is advantageous to assure that there is sufficient overlap between the socket and first end to provide an interference fit for retaining the mouthpiece in a cylindrical shape substantially across its length.

The cylindrical body 2 has a mouthpiece end 8, through which a person would exhale into the spirometer apparatus. It is not essential that the end retain a completely cylindrical shape, as some contouring to the natural shape of a persons' mouth is advantageous in utilizing the mouthpiece without causing discomfort and for assuring a tight seal. However, complete collapse of the mouthpiece end should be avoided and thus the end should have sufficient strength to prevent such collapse during testing.

Preferably, the spirometer tube is formed of a plastic material such as polyethylene, polypropylene, nylon, polyvinylchloride or another suitable plastic. A cardboard or fiberboard type material may also be used with the present invention, though the resilience properties of these materials make them somewhat less satisfactory than a mouthpiece made of a resilient plastic. However, non-resilient materials may be deformed by hand pressure to provide a tube shape which is maintained by the spirometer socket. Some composite materials such as a fiberboard/plastic hybrid material may also be used with the present invention.

The cylindrical body 2 has a pair of longitudinal grooves 9 and 10 which are located at approximately 180° apart. These grooves extend along substantially the entire length of the interior surface of the tube. Preferably, the grooves extend into the wall thickness of the cylindrical body from 10-80% and preferably from 30-65%. Such an extension into the wall thickness assures that the spirometer mouthpiece may collapse into a flat form across these weakening structures i.e., the grooves in the side wall, such that the spirometer mouthpiece may be packaged in flat form.

Figure 2:
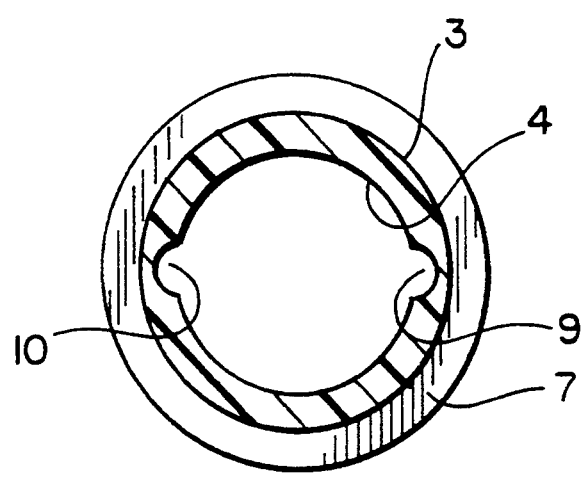
FIG. 2 is a cross sectional view of the spirometer mouthpiece of FIG. 1 taken along line 2—2 of FIG. 1.

Referring to FIG. 2, a cross sectional view of the tube of FIG. 1. is shown with the grooves entering approximately 50% of the wall thickness. For example, a spirometer tube having an outer diameter of approximately 1" and an inner diameter of approximately ¾" has a wall thickness of ⅛". The grooves 9 and 10 have a hemispherical shape and at a center axis of the hemispherical grooves, the depth is about ⅛". Each groove has a width at the inner tube surface of about 3/16". While such hemispherical grooves are shown, it will be understood that square or triangular grooves could additionally be used and the shape of the grooves is unimportant so long as a pair of weakening zones are created on opposite sides of the mouthpiece, preferably at 180° to each other, such that the mouthpiece is collapsible into a flat form.

Utilizing the inventive spirometer mouthpiece, individual packaging in flat form is facilitated.

Figure 3:
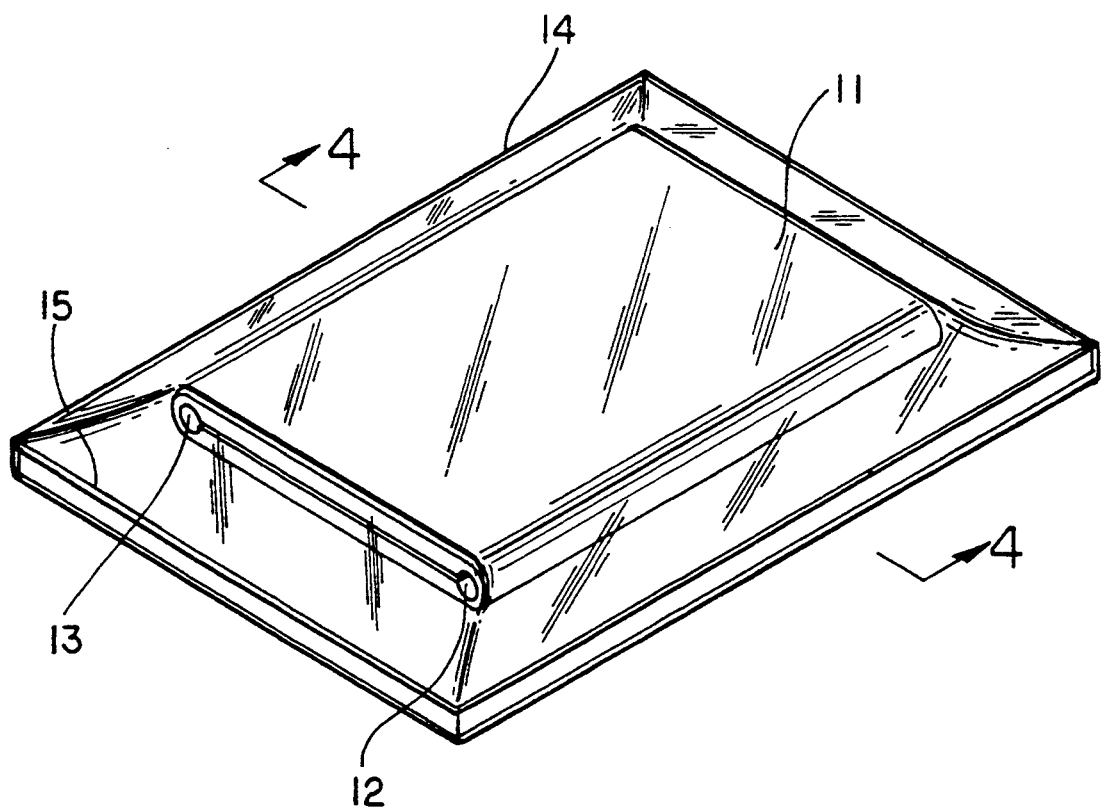
FIG. 3 is a perspective view of the inventive spirometer tube located in a package.

Referring to FIG. 3, a spirometer mouthpiece 11, having a pair of grooves 12 and 13 is shrink wrapped by a film sheet 14, onto a cardboard backing 15, with the shrink wrapping overcoming the resilience, if any, of the mouthpiece, causing the mouthpiece to collapse along the weakening zones on opposite sides of the side wall such that the mouthpiece is presented in flat form. Such packaging allows a plurality of individually packaged mouthpieces to be placed in a box with minimum open space. Additionally, after disposal, the mouthpiece is easily compressed during disposal by the weight of other waste into its flat form to minimize the volume it occupies during disposal.

Figure 4:
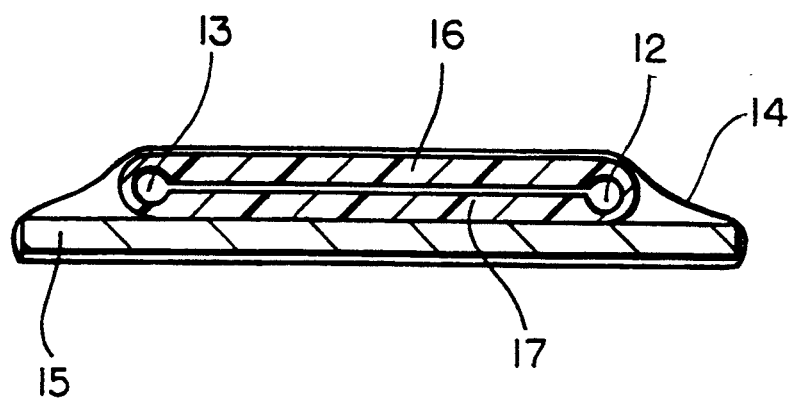
FIG. 4 is a cross sectional view taken along line 4—4 of FIG. 3.

Referring to FIG. 4, the packaged mouthpiece is shown in cross section. When the spirometer tube 11 is compressed, the grooves being weakening structures adapt by relieving the compressive force and allowing the tube to collapse into a pair of substantially parallel walls, 16 and 17. On release from the package, the resilience, if any, of the mouthpiece returns it to its substantially cylindrical form for use. If a non-resilient material is used, light hand pressure easily deforms the mouthpiece into the shape of a tube.

Utilizing the inventive spirometer mouthpiece simplifies packaging for efficient storage utilization, at the same time allowing for individual sterilization of the mouthpieces prior to packaging. Manufacturing at low cost is easily undertaken as a simple cylinder can have a pair of grooves formed during tube molding or extrusion or by machining after tube manufacturing. These are simple low cost operations.

While preferred embodiments of the present invention have been shown and described, it will be understood by those skilled in the art that various changes and modifications could be made without varying from the scope of the present invention.

I claim:

1. A disposable spirometer mouthpiece for directing air into a lung capacity measuring apparatus comprising:

a tubular member having a longitudinal axis and a cylindrical wall, the tubular member having an outer surface and an inner surface, the cylindrical wall having a wall thickness defined by the distance between the inner and outer surfaces, said cylindrical wall having first and second longitudinal zones of reduced thickness, said first and second zones being substantially 180° apart such that the tubular member is collapsible along the first and second zones to reduce the tubular member to a flat state, the tubular member having a first end adapted for mating with the lung capacity measuring apparatus, in an airtight fit, and a second end adapted for use as a mouthpiece, the cylindrical wall having sufficient strength to prevent collapse of the tubular member as air is directed therethrough into the lung capacity measuring apparatus, wherein the tubular member is composed of a plastic material from the group consisting of polyethylene, polypropylene, polyvinylchloride and nylon.

2. The disposable spirometer mouthpiece of claim 1 wherein the first and second longitudinal zones have a reduced thickness of from 20 to 80% of the wall thickness.

3. The disposable spirometer mouthpiece of claim 1 wherein the first and second longitudinal zones are about 50% of the thickness of the cylindrical wall thickness.

4. A disposable spirometer mouthpiece for directing air into a lung capacity measuring apparatus comprising:

a tubular member having a longitudinal axis and a cylindrical wall, the tubular member having an outer surface and an inner surface, the cylindrical wall having an outer surface and an inner surface, the cylindrical wall having a wall thickness defined by the distance between the inner and outer surfaces, said cylindrical wall having first and second longitudinal zones of reduced thickness, said first and second zones being substantially 180° apart such that the tubular member is collapsible along the first and second zones to reduce the tubular member to a flat state, the tubular member having a first end adapted for mating with the lung capacity measuring apparatus, in an airtight fit, and a second end adapted for use as a mouthpiece, the cylindrical wall having sufficient strength to prevent collapse of the tubular member as air is directed therethrough into the lung capacity measuring apparatus, wherein the tubular member is composed of a material from the group consisting of fiberboard, cardboard and fiberboard/plastic hydrids.

5. A packaged disposable spirometer mouthpiece for directing air into a lung capacity measuring apparatus comprising:

a tubular member having a longitudinal axis and a cylindrical wall, the tubular member having an outer surface and an inner surface, the cylindrical wall having a wall thickness defined by the distance between the inner and outer surfaces, said cylindrical wall having first and second longitudinal zones of reduced thickness, said first and second zones being substantially 180° apart such that the tubular member is collapsible along the first and second zones to reduce the tubular member to a flat state, the tubular member having a first end adapted for mating with the lung capacity measuring apparatus, in an airtight fit, and a second end adapted for use as a mouthpiece, the cylindrical wall having sufficient strength to prevent collapse of the tubular member as air is directed therethrough into the lung capacity measuring apparatus, wherein the tubular member is composed of a plastic material, and, packaging means for individually packaging the mouthpiece with sufficient compressive force for storage of the tubular member in a flat form, wherein the packaging means comprise a film disposed over the tubular member and a backing member against which the tubular member is compressed.

* * * * *